(12) United States Patent
Imai et al.

(10) Patent No.: US 9,933,288 B2
(45) Date of Patent: Apr. 3, 2018

(54) PRESSURE DETECTION DEVICE

(71) Applicant: Surpass Industry Co., Ltd., Gyoda-shi, Saitama (JP)

(72) Inventors: Hiroshi Imai, Saitama (JP); Takashi Imai, Saitama (JP)

(73) Assignee: Surpass Industry Co., Ltd., Gyoda-shi, Saitama (JP)

( * ) Notice: Subject to any disclaimer, the term of this patent is extended or adjusted under 35 U.S.C. 154(b) by 0 days.

(21) Appl. No.: 15/420,511

(22) Filed: Jan. 31, 2017

(65) Prior Publication Data
US 2017/0219395 A1 Aug. 3, 2017

(30) Foreign Application Priority Data
Feb. 3, 2016 (JP) .................................. 2016-019245

(51) Int. Cl.
*G01L 7/08* (2006.01)
*G01F 1/38* (2006.01)
(Continued)

(52) U.S. Cl.
CPC ............ *G01F 1/383* (2013.01); *A61M 1/3639* (2013.01); *A61M 1/3672* (2013.01); *G01L 19/0023* (2013.01); *G01L 7/084* (2013.01)

(58) Field of Classification Search
CPC ......... G01F 1/383; G01L 7/08; A61M 1/3639
See application file for complete search history.

(56) References Cited

U.S. PATENT DOCUMENTS 8,079,252 B2 * 12/2011 Weber .................... G01L 23/24
73/114.18
8,857,277 B2 * 10/2014 Huang .................... G01L 9/007
73/728
(Continued)

FOREIGN PATENT DOCUMENTS

DE 2419187 A1 6/1975
DE 203 21 557 U1 1/2008
(Continued)

OTHER PUBLICATIONS

Extended European Search Report dated Jun. 20, 2017 (English Translation).
(Continued)

*Primary Examiner* — Jewel V Dowtin
(74) *Attorney, Agent, or Firm* — Muncy, Geissler, Olds & Lowe, P.C.

(57) ABSTRACT

The flow channel unit includes: a pair of end flow channels disposed at an inflow port and an outflow port, respectively, and extending along in flow direction; a center flow channel including a pressure receiving portion having a thin film shape and disposed at a position sandwiched between the pair of end flow channels, a distance from an inner peripheral surface of the pressure receiving portion to an outer peripheral surface thereof being shorter than a distance from an inner peripheral surface of the pair of end flow channels to an outer peripheral surface thereof. The pair of end flow channels and the center flow channel are integrally formed of a flexible resin material, and the pressure detection portion is disposed such that the pressure of the fluid circulated through a flow channel is transmitted via the pressure receiving portion.

7 Claims, 10 Drawing Sheets

(51) Int. Cl.
    *A61M 1/36*     (2006.01)
    *G01L 19/00*     (2006.01)

(56) References Cited

U.S. PATENT DOCUMENTS

| | | |
|---|---|---|
| 2002/0194924 A1 | 12/2002 | Ozawa |
| 2005/0160828 A1 | 7/2005 | Hasunuma |
| 2008/0110267 A1* | 5/2008 | Sheikh-Bahaie ... B60C 23/0408 73/700 |
| 2008/0229838 A1 | 9/2008 | Kleven et al. |
| 2013/0073225 A1* | 3/2013 | Huang ............ G01L 9/14 702/50 |
| 2014/0076058 A1 | 3/2014 | Brugger et al. |
| 2017/0028119 A1 | 2/2017 | Brugger et al. |

FOREIGN PATENT DOCUMENTS

| | | |
|---|---|---|
| JP | 2005-207946 A | 8/2005 |
| WO | WO 2008/115346 A2 | 9/2008 |

OTHER PUBLICATIONS

Partial European Search Report dated Jun. 23, 2017 (English Translation).

\* cited by examiner

PRESSURE DETECTION DEVICE

CROSS-REFERENCE TO RELATED APPLICATIONS

This application is based on Japanese Patent Application No. 2016-019245, the contents of which are incorporated herein by reference in its entirety.

TECHNICAL FIELD

The present disclosure relates to a pressure detection device that detects a pressure of a fluid circulated through a flow channel.

BACKGROUND ART

An in-line type pressure sensor having a structure in which a body provided with a flow channel for circulating a liquid, such as a drug solution, and a sensor body for detecting a pressure of liquid transmitted to a pressure receiving surface through a protector are integrally formed has been conventionally known (for example, see Japanese Unexamined Patent Application, Publication No. 2005-207946 (hereinafter referred to as "JP 2005-207946")).

The pressure sensor disclosed in JP 2005-207946 detects the pressure of the fluid transmitted to the sensor body through the protector attached to a lower surface of the sensor body.

Technical Problem

The pressure sensor disclosed in JP 2005-207946 can obtain a detected value corresponding to a pressure at which the fluid presses the protector when the protector is pressed against the lower surface of the sensor body by the pressure of the fluid.

However, in the pressure sensor disclosed in JP 2005-207946, a fluid introduction portion formed in the body is sealed with the sensor body, so that a small amount of fluid may accumulate in a space between the sensor body and the body. If the fluid is a coagulable fluid, such as blood, there is a possibility that an accumulated and solidified fluid may be recirculated through the flow channel.

The present disclosure has been made in view of the above-mentioned circumstances, and an object of the present disclosure is to provide a pressure detection device capable of detecting a pressure of a fluid circulated through a flow channel, while preventing the occurrence of a malfunction due to the accumulation of the fluid in the flow channel.

Solution to Problem

In order to solve the above-mentioned problem, the present disclosure employs the following solutions.

A pressure detection device according to one aspect of the present disclosure includes: a pressure detection unit configured to detect a pressure to be transmitted to a pressure detection portion; and a flow channel unit including a flow channel body provided with a flow channel through which a fluid is circulated along a circulation direction from an inflow port to an outflow port. The flow channel body includes: a pair of end flow channels disposed at the inflow port and the outflow port, respectively; and a center flow channel including a pressure receiving portion having a thin film shape and disposed at a position sandwiched between the pair of end flow channels, a distance from an inner peripheral surface of the pressure receiving portion to an outer peripheral surface thereof being shorter than a distance from an inner peripheral surface of the pair of end flow channels to an outer peripheral surface thereof. The pair of end flow channels and the center flow channel are integrally formed of a flexible resin material. The pressure detection portion is disposed in such a manner that the pressure of the fluid circulated through the flow channel is transmitted via the pressure receiving portion.

In the pressure detection device according to one aspect of the present disclosure, the pair of end flow channels and the center flow channel disposed at a position sandwiched between the pair of end flow channels are integrally formed of a flexible resin material. Accordingly, the flow channel body included in the pressure detection device according to one aspect of the present disclosure has no portion where a part of the portion is sealed with another member, so that a small amount of fluid does not accumulate on the sealed portion. Accordingly, even when a coagulable fluid, such as blood, is circulated, a malfunction that an accumulated and solidified fluid is recirculated through the flow channel can be prevented.

Further, in the pressure detection device according to one aspect of the present disclosure, the center flow channel includes the pressure receiving portion having a thin film shape. The pressure detection portion is disposed in such a manner that the pressure of the fluid circulated through the flow channel is transmitted via the pressure receiving portion having a thin film shape. Therefore, in the pressure detection device according to one aspect of the present disclosure, the pressure detection portion can appropriately detect the pressure of the fluid transmitted via the pressure receiving portion having a thin film shape.

Thus, according to the pressure detection device of one aspect of the present disclosure, it is possible to provide a pressure detection device capable of detecting a pressure of a fluid circulated through a flow channel, while preventing the occurrence of a malfunction due to the accumulation of the fluid in the flow channel.

In the pressure detection device according to one aspect of the present disclosure, the center flow channel may have a structure in which a distance from an inner peripheral surface in a partial region of the center flow channel in a circumferential direction about the circulation direction to an outer peripheral surface thereof is shorter than a distance from an inner peripheral surface in another region of the center flow channel to an outer peripheral surface thereof, and the partial region is set as the pressure receiving portion.

With this structure, the partial region of the center flow channel in the circumferential direction is set as a region in which a displacement in the pressure of the fluid is more likely to occur than in the other region. The partial region is set as the pressure receiving portion, thereby making it possible to appropriately detect the pressure of the fluid.

In the pressure detection device according to one aspect of the present disclosure, the center flow channel has a flow channel sectional area larger than that of the pair of end flow channels. A pair of connecting flow channels is formed to connect an end of the pair of end flow channels that is located closer to the center flow channel and both ends of the center flow channel. The pair of end flow channels, the center flow channel, and the pair of connecting flow channels are integrally formed of a flexible resin material. The pair of connecting flow channels is formed in such a manner that a flow channel sectional area of the pair of connecting flow channels gradually increases toward the both ends of the center flow channel.

In the pressure detection device having a structure as described above, the pair of connecting flow channels connects the pair of end flow channels and the center flow channel so that the flow channel sectional area gradually increases toward both ends of the center flow channel from the pair of end flow channels. Therefore, when the fluid is circulated from the end flow channel disposed at the inflow port to the center flow channel, the fluid does not accumulate on the flow channel. Further, when the fluid is circulated from the center flow channel to the end flow channel where the outflow port is disposed, the fluid does not accumulate on the flow channel.

The pressure detection device according to one aspect of the present disclosure may have a structure in which the pressure detection unit includes: a pressure sensor including the pressure detection portion; and a pressure transmission portion disposed in a state where one end of the pressure transmission portion is in contact with the pressure detection portion and the other end of the pressure transmission portion is in contact with the pressure receiving portion, the pressure transmission portion being configured to transmit the pressure of the fluid received by the pressure receiving portion to the pressure detection portion, and the pressure transmission portion may displace the pressure receiving portion toward the flow channel and may be disposed in a state of receiving an urging force directed to the pressure detection portion from the pressure receiving portion.

According to the pressure detection device having a structure as described above, the pressure transmission portion disposed in a state where one end of the pressure transmission portion is in contact with the pressure detection portion and the other end thereof is in contact with the pressure receiving portion of the flow channel unit is disposed in a state of receiving an urging force directed to the pressure detection portion from the pressure receiving portion. Accordingly, even when the pressure of the fluid circulated through the flow channel is temporarily reduced and becomes a negative pressure, the pressure detection portion is in a state of receiving a pressure having a value obtained by subtracting a negative pressure value corresponding to a negative pressure from a pressure value equivalent to the urging force received by the pressure transmission portion from the pressure receiving portion. Thus, even when the pressure of the fluid is temporarily reduced and becomes a negative pressure, the pressure detection portion can obtain a pressure value obtained by subtracting a decrease in the pressure value corresponding to the negative pressure from the pressure value equivalent to the urging force received from the pressure receiving portion.

In the pressure detection device having a structure described above, the flow channel unit may be provided with a recess in which the pressure receiving portion is disposed; the pressure sensor may be disposed in contact with the flow channel unit so as to cover the recess; and a communication flow channel may be formed to allow an inside space and an outside space to communicate with each other, the inside space and the outside space being partitioned by the recess and the pressure sensor.

With this structure, it is possible to suppress the occurrence of a malfunction that the inside space partitioned by the pressure sensor and the recess in which the pressure receiving portion of the flow channel unit is disposed communicates with the outside space and the volume of the inside space fluctuates according to the displacement of the pressure receiving portion, which causes a fluctuation in the pressure of the inside space.

The pressure detection device having a structure as described above may have an aspect in which the pressure transmission portion includes: a first pressure transmission member disposed in contact with the pressure receiving portion; and a second pressure transmission member disposed in contact with the pressure detection portion, and a contact area between the second pressure transmission member and the pressure detection portion is smaller than a contact area between the first pressure transmission member and the pressure receiving portion.

With this structure, the fluid pressure received by the first pressure transmission member from the pressure receiving portion can be transmitted in such a manner that the fluid pressure is locally concentrated on the pressure detection portion via the second pressure transmission member having a small contact area with an opposed member. Accordingly, the fluctuation in the pressure locally received by the pressure detection portion is increased with respect to the fluctuation in the fluid pressure, thereby making it possible to increase the accuracy of detecting the fluctuation in the fluid pressure.

The pressure detection device according to the above aspect may have an aspect in which the first pressure transmission member is a member formed into a spherical shape projecting toward the pressure receiving portion.

With this structure, the contact area where the first transmission member contacts the pressure receiving portion is maintained substantially constant, regardless of the displacement in the pressure receiving portion, and thus the accuracy of transmitting the pressure of the fluid from the pressure receiving portion to the first transmission member can be increased.

In the pressure detection device according to the above aspect, the second pressure transmission member may be a member formed into a spherical shape projecting toward the pressure detection portion.

With this structure, the fluid pressure received by the first pressure transmission member from the pressure receiving portion can be transmitted in such a manner that the fluid pressure is locally concentrated on the pressure detection portion via the second pressure transmission member formed into a spherical shape. Accordingly, the fluctuation in the pressure locally received by the pressure detection portion is increased with respect to the fluctuation in the fluid pressure, and thus the accuracy of detecting the fluctuation in the fluid pressure can be increased.

The pressure detection device according to one aspect of the present disclosure may have a structure in which the pressure transmission portion is disposed in contact with both the pressure receiving portion and the pressure detection portion, and is formed into a spherical shape.

With this structure, the contact area where the pressure transmission portion contacts the pressure receiving portion is maintained substantially constant, regardless of the displacement in the pressure receiving portion, and thus the accuracy of transmitting the pressure of the fluid from the pressure receiving portion to the pressure transmission portion can be increased.

Further, the fluid pressure received by the pressure transmission portion from the pressure receiving portion can be transmitted in such a manner that the fluid pressure is locally concentrated on the pressure detection portion via the pressure transmission portion formed into a spherical shape. Accordingly, the fluctuation in the pressure locally received by the pressure detection portion is increased with respect to the fluctuation in the fluid pressure, and thus the accuracy of detecting the fluctuation in the fluid pressure can be increased.

Advantageous Effects

According to the present disclosure, it is possible to provide a pressure detection device capable of detecting a pressure of a fluid circulated through a flow channel, while preventing the occurrence of a malfunction due to the accumulation of the fluid in the flow channel.

DESCRIPTION OF EMBODIMENTS

First Embodiment

A pressure detection device 100 according to a first embodiment of the present disclosure will be described below with reference to the drawings.

Figure 1:
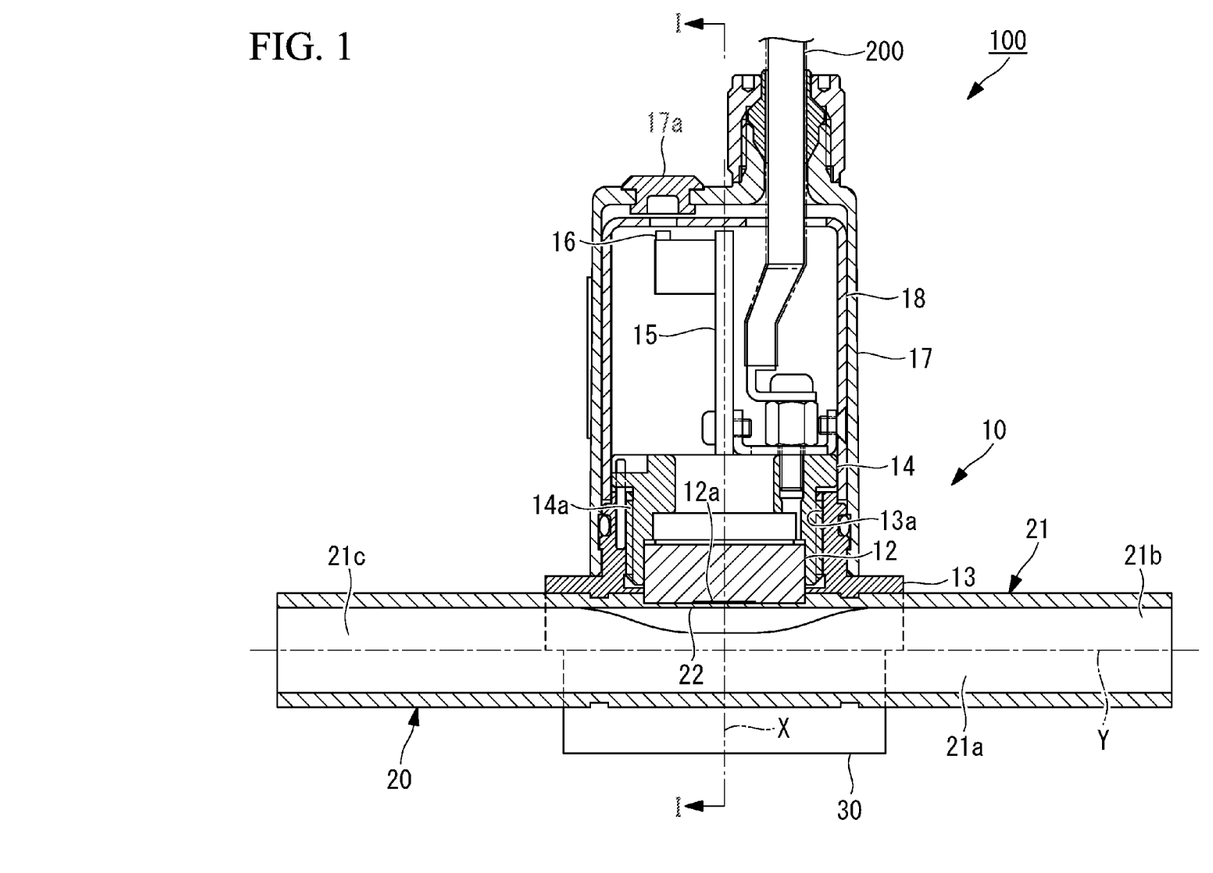
FIG. 1 is a longitudinal sectional view showing a pressure detection device of a first embodiment.

As shown in FIG. 1, the pressure detection device 100 of the first embodiment includes: a pressure detection unit 10 for detecting a pressure of a fluid; a flow channel unit 20 including a flow channel body 21 having a flow channel 21a formed therein; and a base portion 30 which is attached in a state where the flow channel unit 20 is sandwiched between the pressure detection unit 10 and the base portion 30. The flow channel 21a is a flow channel through which the fluid is circulated along a linear circulation direction from an inflow port 21b to an outflow port 21c.

Figure 2:
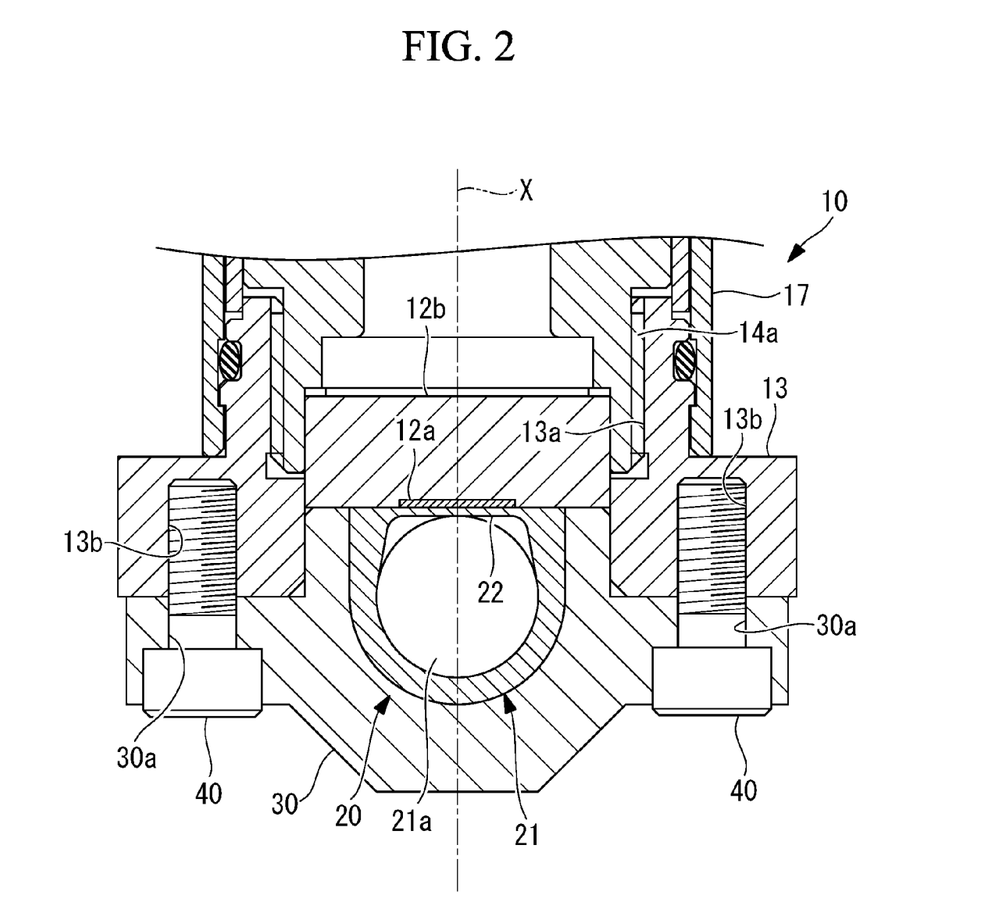
FIG. 2 is a sectional view taken along a line I-I of the pressure detection device shown in FIG. 1.

As shown in FIG. 2, the base portion 30 is connected to a body portion 13 in such a manner that a fastening bolt 40 which is inserted from a fastening hole 30a which is formed in the base portion 30 is fastened to a fastening hole 13b which is formed in the body portion 13.

The pressure detection unit 10 shown in FIG. 1 is a device that detects a pressure to be transmitted to a diaphragm 12a (pressure detection portion).

As shown in FIG. 1, the pressure detection unit 10 includes: a pressure sensor 12 that detects the pressure of the fluid transmitted from the flow channel body 21; the body portion 13 that accommodates the pressure sensor 12; a sensor holding portion 14 that holds the pressure sensor 12 in a state where the pressure sensor 12 is disposed in the body portion 13; a sensor substrate 15 for transmitting power and an electric signal between the pressure sensor 12 and a cable 200 connected to an external device (not shown); a zero point adjustment switch 16 for performing zero point adjustment of the pressure sensor 12; and a housing 17 that accommodates the sensor substrate 15.

The components included in the pressure detection unit 10 will be described below.

The pressure sensor 12 includes: the diaphragm 12a (pressure detection portion), which is formed into a thin film shape using a material (for example, sapphire) having a corrosion resistance; a strain resistance (not shown) which is attached to the diaphragm 12a; and a base portion 12b which holds the diaphragm 12a. The pressure sensor 12 is a strain sensor that outputs a pressure signal corresponding to the strain resistance that varies depending on the pressure transmitted to the diaphragm 12a.

The body portion 13 is a member having a structure in which an upper member formed into a cylindrical shape about an axis line X and a lower member that accommodates the flow channel unit 20 are integrally formed. On the inner peripheral surface at an upper side of the body portion 13, a female screw 13a for attaching the sensor holding portion 14 to be described later is formed.

As shown in FIG. 2, at a lower end of the body portion 13, fastening holes 13b are formed at a plurality of locations about the axis line X. In a state where the flow channel unit 20 is disposed at a lower end of the body portion 13 and the base portion 30 is disposed at a lower end of the flow channel unit 20, the fastening bolts 40 inserted from the fastening holes 30a of the base portion 30 are fastened to the fastening holes 13b. In a state where the base portion 30 is attached to the body portion 13, the pressure sensor 12 is inserted into a central portion of the body portion 13 from above along the axis line X.

The sensor holding portion 14 is a member formed into a cylindrical shape about the axis line X, and a male screw 14a is formed on an outer peripheral surface of the sensor holding portion 14. The sensor holding portion 14 holds the pressure sensor 12 at a predetermined position with respect to the body portion 13 in such a manner that the pressure sensor 12 is disposed on the inner peripheral side of the lower end of the body portion 13 and the male screw 14a formed on the outer peripheral surface is fastened to the female screw 13a which is formed in the inner peripheral surface of the body portion 13.

The sensor substrate 15 includes, for example, an amplifier circuit (not shown) which amplifies a pressure signal output from the pressure sensor 12; an interface circuit which transmits the pressure signal amplified by the amplifier circuit to a pressure signal line (not shown) of the cable 200; a power supply circuit (not shown) which transmits a power supply voltage supplied from the outside via the cable 200 to the pressure sensor 12; and a zero point adjustment circuit (not shown) which performs zero point adjustment when the zero point adjustment switch 16 is pressed.

The zero point adjustment switch 16 is a switch which is turned on when an operator presses a pressing portion 17a which is provided on an upper surface of the housing 17. When the zero point adjustment switch 16 is turned on, the zero point adjustment circuit adjusts the pressure signal output from the pressure sensor 12 at that time to be set as an initial value (zero).

This operation is a manipulation necessary at the time of starting the measurement of the pressure signal after the pressure detection device 100 is assembled. This is because it is necessary to preliminarily set, as a pressure detection value zero, a state in which an urging force from a pressure transmission portion 11 is supplied to the pressure sensor 12 so that the pressure detection device 100 can measure a negative pressure. Thus, even when the urging force supplied to the pressure sensor 12 by the pressure transmission portion 11 varies depending on the individual pressure detection device 100, the state in which the pressure detection value is zero can be appropriately set and the pressure can be accurately measured.

The housing 17 is a member formed into a cylindrical shape about the axis line X, and the inner peripheral surface at the lower end of the housing 17 is attached to the outer peripheral surface on the upper end side of the body portion 13. The housing 17 accommodates the sensor substrate 15 in the inner peripheral side thereof.

The inside cover 18 is a cylindrical member which is disposed in the housing 17 and has an inner peripheral surface disposed in contact with the outer peripheral surface of the upper portion of the sensor holding portion 14. The outer peripheral surface of the inside cover 18 about the axis line X is disposed in contact with the inner peripheral surface of the housing 17.

Next, the flow channel unit 20 will be described in detail with reference to the drawings.

An inflow pipe (not shown) through which the fluid is caused to flow into the inflow port 21*b* is attached to the inflow port 21*b* of the flow channel unit 20, and an outflow pipe (not shown) for circulating the fluid flowing from the outflow port 21*c* is attached to the outflow port 21*c* of the flow channel unit 20. The pressure of the fluid circulated through the flow channel 21*a* from the inflow port 21*b* toward the outflow port 21*c* is detected by the pressure detection unit 10.

The fluid described herein refers to, for example, a liquid such as blood or dialysis fluid.

The flow channel body 21 is a member integrally formed of a flexible resin material such as silicon, PVC, or PFA. The flow channel body 21 is provided with a recess 21*d* which has a circular planar shape.

Figure 3:
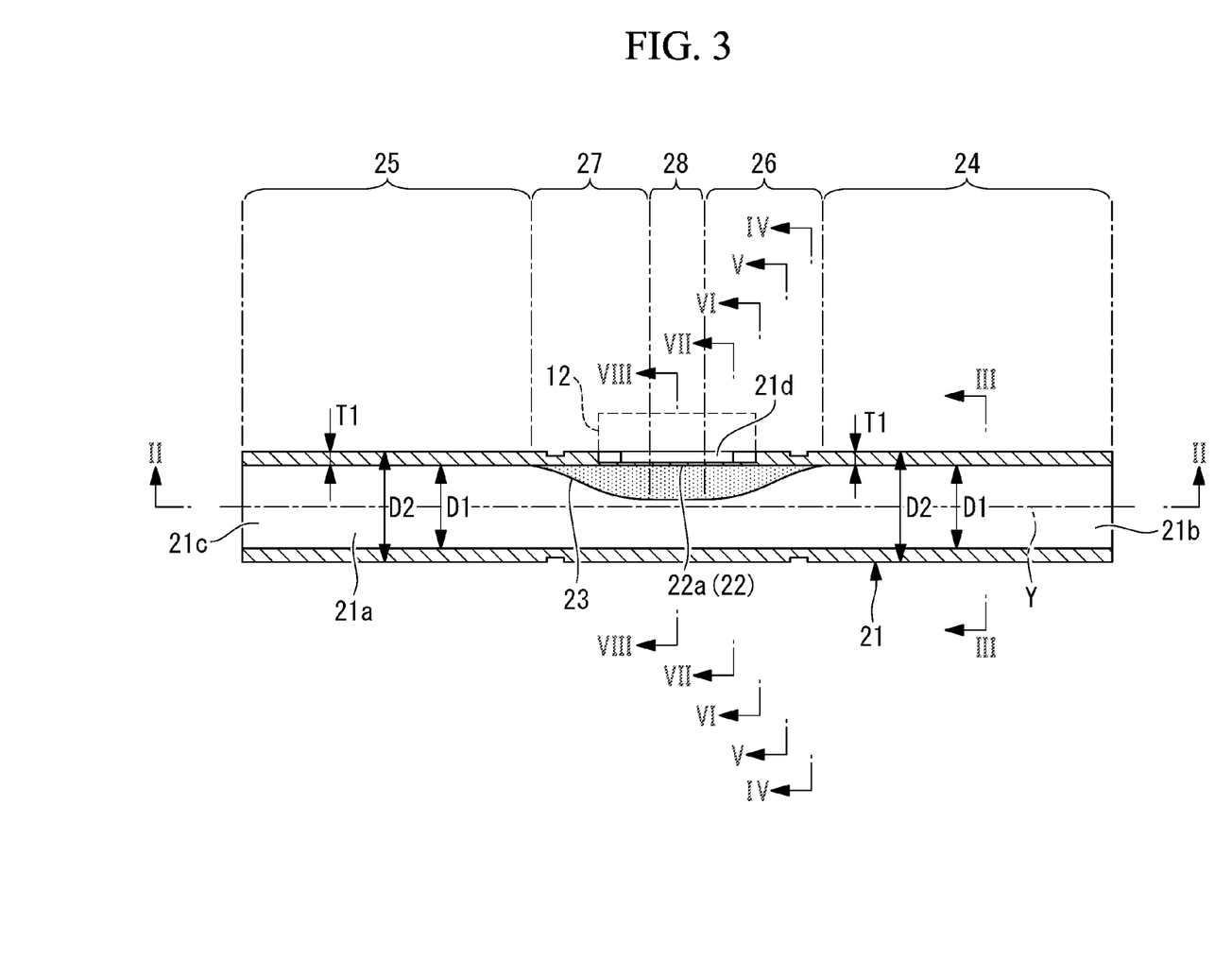
FIG. 3 is a longitudinal sectional view showing a flow channel body shown in FIG. 1.

As shown in FIG. 3, a portion where the recess 21*d* of the flow channel body 21 is formed corresponds to a central portion 22*a* of the diaphragm 22 (pressure receiving portion). The central portion 22*a* is formed into a thin film shape with a flow channel thickness T2. The pressure sensor 12 is disposed in the recess 21*d* in such a manner that the diaphragm 12*a* contacts the outer peripheral surface of the diaphragm 22.

Since the central portion 22*a* of the diaphragm 22 is formed into a thin film shape, the central portion 22*a* receives the pressure of the fluid, which is circulated through the flow channel 21*a*, and is displaced in the direction along the axis line X. The diaphragm 12*a* of the pressure sensor 12 is disposed so as to transmit the pressure of the fluid circulated through the flow channel 21*a* via the diaphragm 22.

Figure 4:
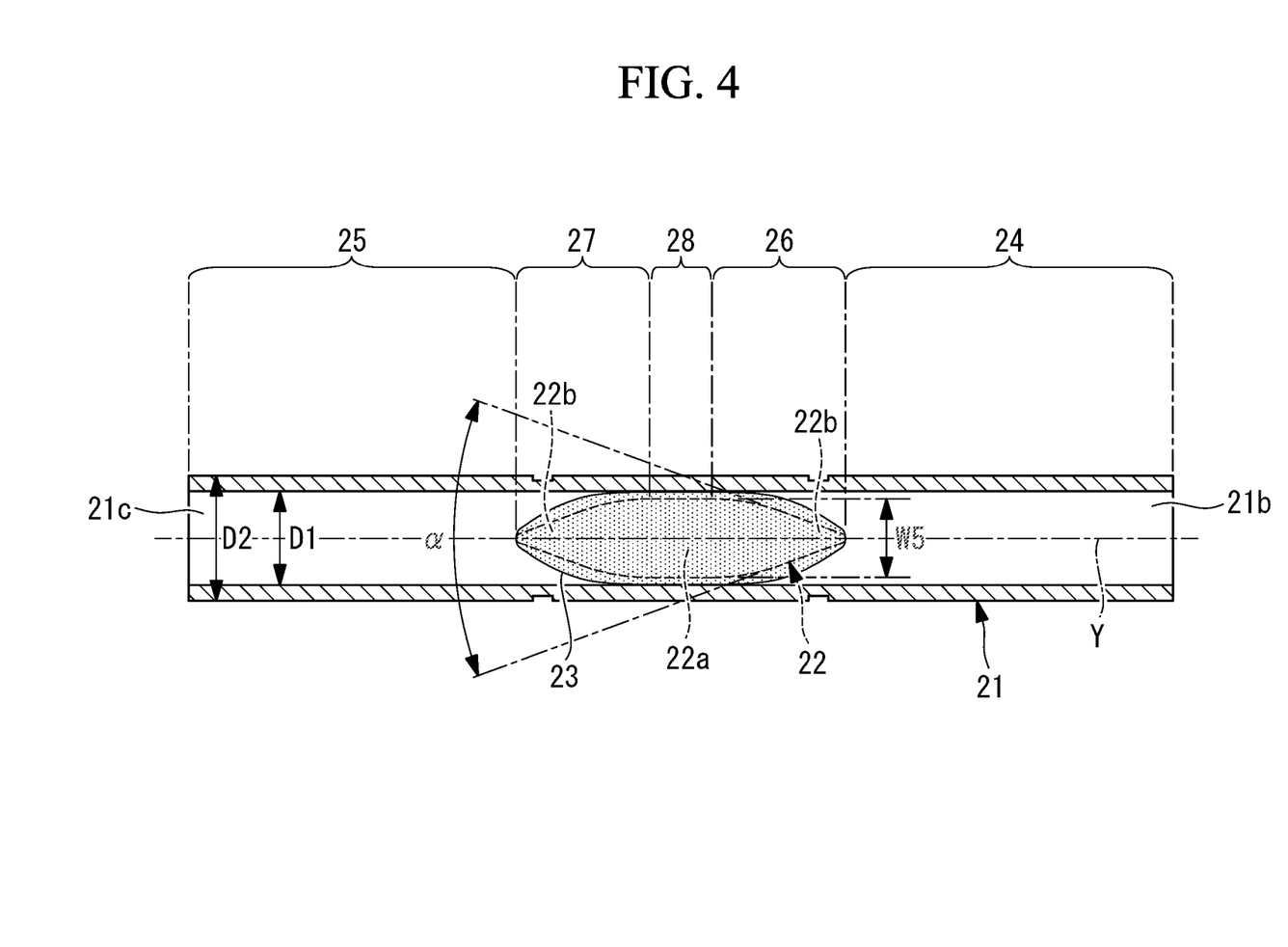
FIG. 4 is a sectional view taken along a line II-II of the flow channel body shown in FIG. 3.

As shown in FIGS. 3 and 4, the flow channel body 21 includes: an inflow-side end flow channel 24 disposed at the inflow port 21*b*; an outflow-side end flow channel 25 disposed at the outflow port 21*c*; a center flow channel 28 disposed at a position sandwiched between the inflow-side end flow channel 24 and the outflow-side end flow channel 25; an inflow-side connecting flow channel 26 formed so as to connect the center flow channel 28 and an end of the inflow-side end flow channel 24 that is located closer to the center flow channel 28; and an outflow-side connecting flow channel 27 formed so as to connect the center flow channel 28 and an end of the outflow-side end flow channel 25 that is located closer to the center flow channel 28.

The pair of end flow channels (the inflow-side end flow channel 24 and the outflow-side end flow channel 25), the pair of connecting flow channels (the inflow-side connecting flow channel 26 and the outflow-side connecting flow channel 27), and the center flow channel 28 are integrally formed (integrally molded) of the above-mentioned flexible resin material. These flow channels are integrally molded and formed as a single member, so that there is no connected portion, such as a seam, at each portion where these flow channels are connected.

The inflow-side end flow channel 24 is a flow channel having an inner peripheral surface and an outer peripheral surface which are formed in a cylindrical shape extending along an axis line Y. As shown in FIG. 3, an inner diameter D1 and an outer diameter D2 of the inflow-side end flow channel 24 are constant in a range from the inflow port 21*b* to the inflow-side connecting flow channel 26.

Figure 6:
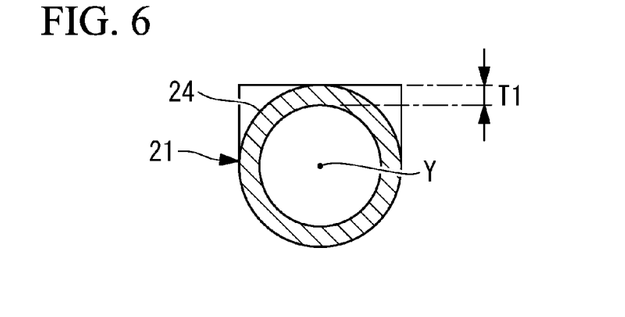
FIG. 6 is a sectional view taken along a line III-III of the flow channel body shown in FIG. 3.

As shown in FIG. 6 (which is a sectional view taken along a line III-III of the flow channel body 21 shown in FIG. 3), a flow channel thickness T1 which is a distance from the inner peripheral surface of the inflow-side end flow channel 24 to the outer peripheral surface thereof is constant over the perimeter in the circumferential direction about the axis line Y.

The outflow-side end flow channel 25 is a flow channel having an inner peripheral surface and an outer peripheral surface which are formed into a cylindrical shape extending along the axis line Y. As shown in FIG. 3, the inner diameter D1 and the outer diameter D2 of the outflow-side end flow channel 25 are constant in a range from the outflow-side connecting flow channel 27 to the outflow port 21*c*.

Like the inflow-side end flow channel 24, the flow channel thickness T1 which is a distance from the inner peripheral surface of the outflow-side end flow channel 25 to the outer peripheral surface thereof is constant over the perimeter in the circumferential direction about the axis line Y.

In FIG. 3, a shaded region indicates a recess 23. The distance from the axis line Y, which is at the center of the flow channel 21*a*, to the inner peripheral surface of the flow channel body 21 is longer than D1/2.

A flow channel sectional area of the flow channel 21*a* is constant at each position in the circulation direction in both the inflow-side end flow channel 24 and the outflow-side end flow channel 25. On the other hand, the flow channel sectional area of each of the inflow-side connecting flow channel 26, the outflow-side connecting flow channel 27, and the center flow channel 28 is larger than that of the inflow-side end flow channel 24 and the outflow-side end flow channel 25.

More specifically, the flow channel sectional area at each position in the circulation direction gradually increases toward the center flow channel 28 in the inflow-side connecting flow channel 26 which is directed from the inflow-side end flow channel 24 to the center flow channel 28. Further, the flow channel sectional area at each position in the circulation direction gradually increases toward the center flow channel 28 in the outflow-side connecting flow channel 27 which is directed from the outflow-side end flow channel 25 to the center flow channel 28.

Thus, the flow channel sectional area at each position of the flow channel 21a gradually increases toward the center flow channel 28 from the inflow-side end flow channel 24 and gradually decreases toward the outflow-side end flow channel 25 from the center flow channel 28. This is because the recess 23 is formed in each of the inflow-side connecting flow channel 26, the outflow-side connecting flow channel 27, and the center flow channel 28.

The inflow-side connecting flow channel 26 is a flow channel which connects an end of the inflow-side end flow channel 24 that is located closer to the outflow port 21c and an end of the center flow channel 28 that is located closer to the inflow port 21b. The flow channel sectional area of the inflow-side connecting flow channel 26 gradually increases toward the center flow channel 28 from the inflow-side end flow channel 24.

As shown in FIGS. 7 to 10, on a surface (upper surface in each figure) of the inflow-side connecting flow channel 26 that is located closer to the pressure sensor 12, an end 22b of the diaphragm 22 having a flat inner peripheral surface is formed. The width of the end 22b in the horizontal direction at each position on the axis line Y gradually increases toward the center flow channel 28 from the inflow-side end flow channel 24.

Figure 7:
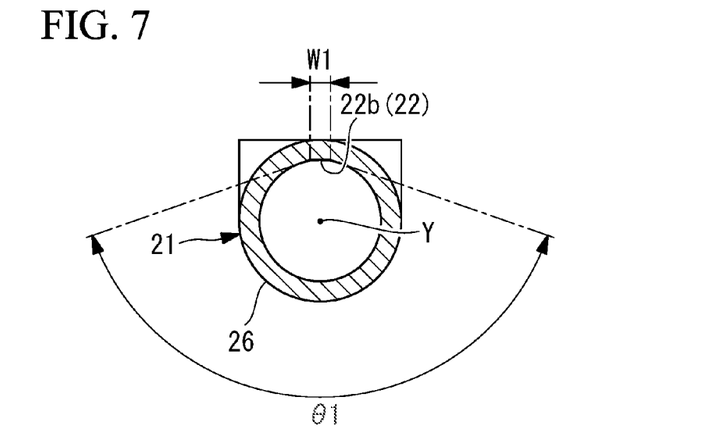
FIG. 7 is a sectional view taken along a line IV-IV of the flow channel body shown in FIG. 3.
Figure 8:
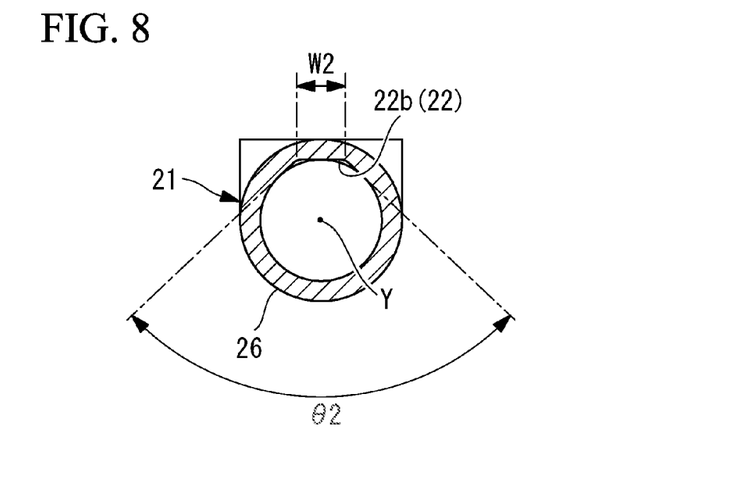
FIG. 8 is a sectional view taken along a line V-V of the flow channel body shown in FIG. 3.
Figure 9:
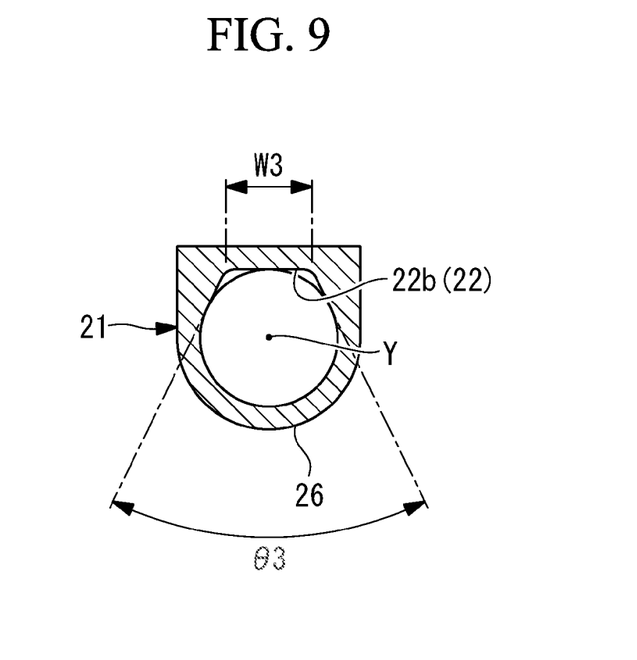
FIG. 9 is a sectional view taken along a line VI-VI of the flow channel body shown in FIG. 3.
Figure 10:
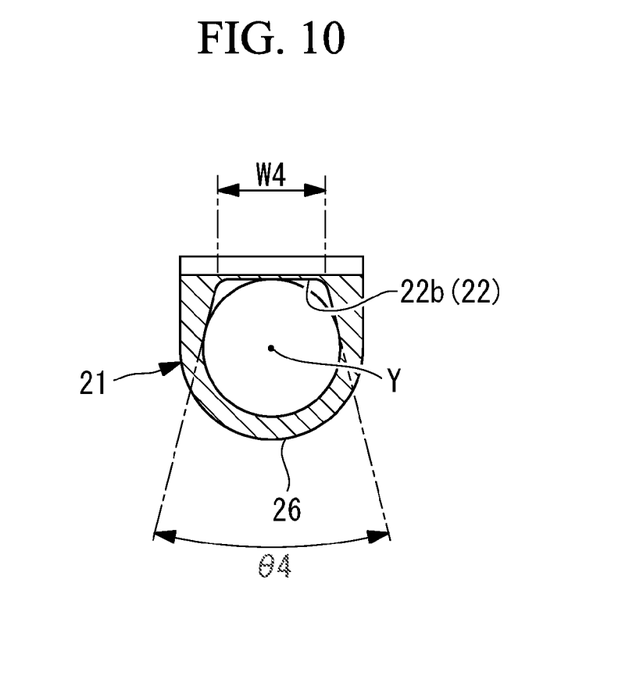
FIG. 10 is a sectional view taken along a line VII-VII of the flow channel body shown in FIG. 3.

At a position on the axis line Y shown in FIG. 7 (which is a sectional view taken along a line IV-IV of the flow channel body 21 shown in FIG. 3), the width of the end 22b of the diaphragm 22 is represented by W1. At a position on the axis line Y shown in FIG. 8 (which is a sectional view taken along a line V-V of the flow channel body 21 shown in FIG. 3), the width of the end 22b of the diaphragm 22 is represented by W2. At a position on the axis line Y shown in FIG. 9 (which is a sectional view taken along a line VI-VI of the flow channel body 21 shown in FIG. 3), the width of the end 22b of the diaphragm 22 is represented by W3. At a position on the axis line Y shown in FIG. 10 (which is a sectional view taken along a line VII-VII of the flow channel body 21 shown in FIG. 3), the width of the end 22b of the diaphragm 22 is represented by W4.

As shown in each figure, the width of the diaphragm 22 in the horizontal direction at each position on the axis line Y gradually increases in the order of W1, W2, W3, and W4 toward the center flow channel 28 from the inflow-side end flow channel 24.

The outflow-side connecting flow channel 27 is a flow channel which connects an end of the outflow-side end flow channel 25 that is located closer to the inflow port 21b and an end of the center flow channel 28 that is located closer to the outflow port 21c. The flow channel sectional area of the outflow-side connecting flow channel 27 gradually increases toward the center flow channel 28 from the outflow-side end flow channel 25.

On a surface of the outflow-side connecting flow channel 27 that is located closer to the pressure sensor 12, the end 22b of the diaphragm 22 having a flat inner peripheral surface is formed. Although not shown, the width of the end 22b in the horizontal direction at each position on the axis line Y gradually increases toward the center flow channel 28 from the outflow-side end flow channel 25.

The shape of the outflow-side connecting flow channel 27 is similar to the inflow-side connecting flow channel 26, except that the direction in which the flow channel sectional area increases is opposite to the circulation direction.

Figure 5:
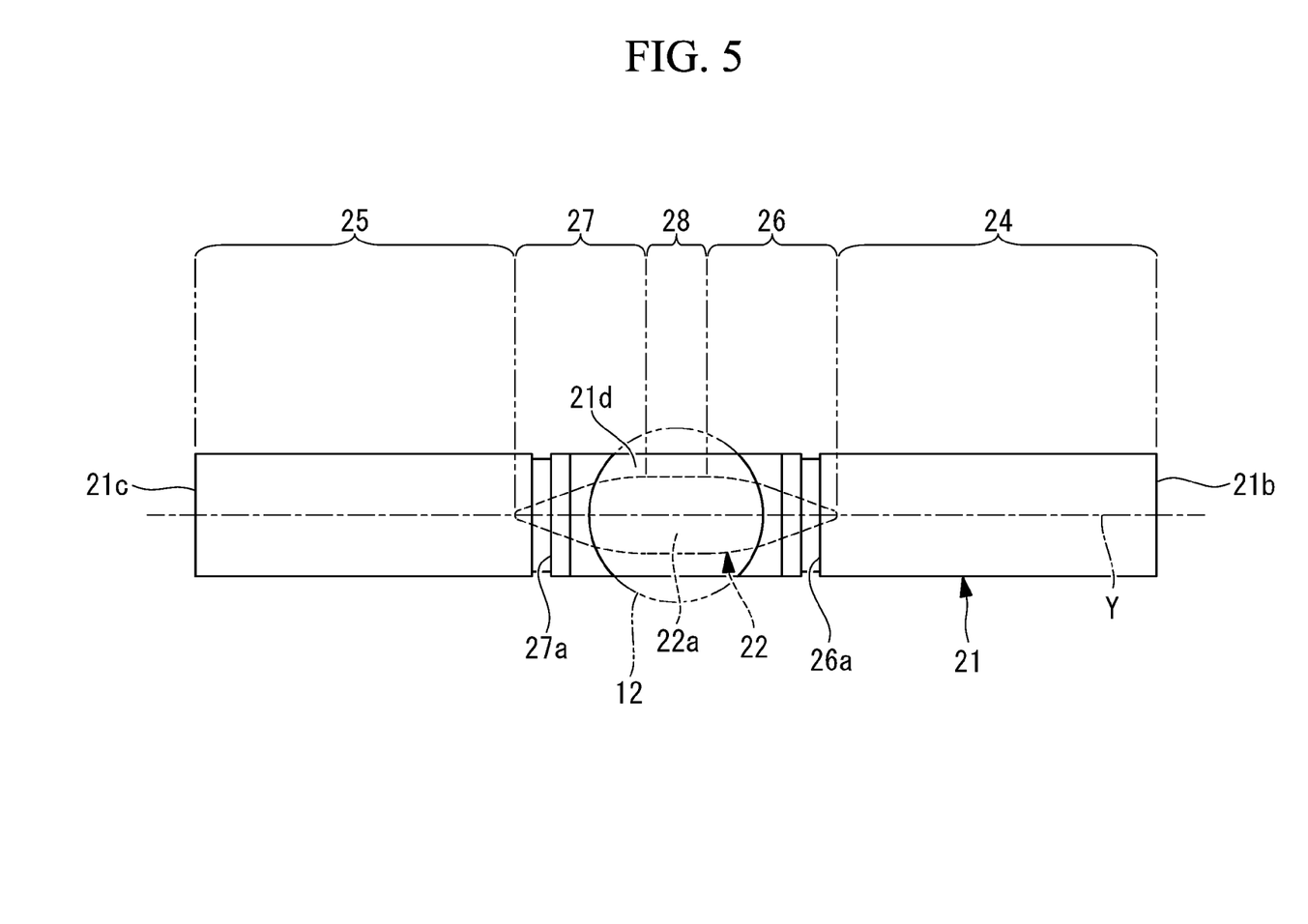
FIG. 5 is a plan view of the flow channel body shown in FIG. 1.

As shown in FIG. 5, the inflow-side connecting flow channel 26 and the outflow-side connecting flow channel 27 are respectively provided with an annular groove 26a and an annular groove 27a which are formed into an annular shape about the axis line Y.

The annular groove 26a and the annular groove 27a are caused to engage with annular projections which are formed at positions respectively corresponding to the body portion 13 and the base portion 30, thereby fixing the position of the flow channel body 21 on the axis line Y.

Figure 11:
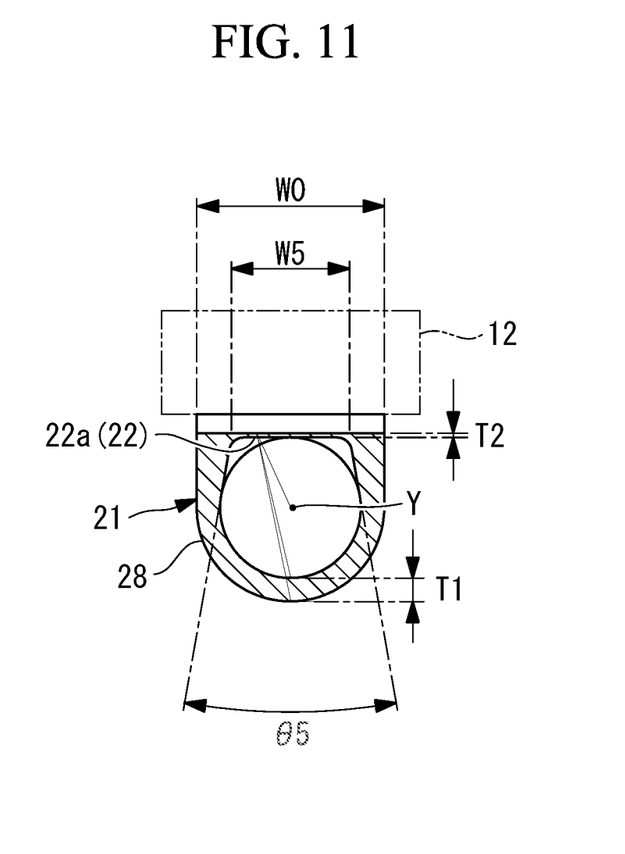
FIG. 11 is a sectional view taken along a line VIII-VIII of the flow channel body shown in FIG. 3.

As shown in FIG. 11, the distance (flow channel thickness T2) from the inner peripheral surface in a region at a lower end side of the center flow channel 28 in the circumferential direction about the axis line Y, which is the circulation direction, to the outer peripheral surface thereof is shorter than the distance (flow channel thickness T1) from the inner peripheral surface in another region to the outer peripheral surface. As shown in FIG. 11, a region at a lower end of the center flow channel 28 corresponds to the central portion 22a of the diaphragm 22 having thin film shape.

On a surface (an upper surface in FIG. 11) of the center flow channel 28 that is located closer to the pressure sensor 12, the central portion 22a of the diaphragm 22 having a flat inner peripheral surface is formed. The width of the central portion 22a in the horizontal direction at each position on the axis line Y is represented by W5 and is constant. The thickness of the central portion 22a at each position on the axis line Y is represented by the flow channel thickness T2 and is constant.

Thus, the center flow channel 28 includes the central portion 22a of the diaphragm 22 having a thin film shape. The distance (flow channel thickness T2) from the inner peripheral surface of the central portion 22a to the outer peripheral surface thereof is shorter than the distance (flow channel thickness T1) from the inner peripheral surface of each of the inflow-side end flow channel 24 and the outflow-side end flow channel 25 to the outer peripheral surface thereof.

As shown in FIG. 4, a part of the recess 23 formed in the inner peripheral surface of the flow channel body 21 that is located closer to the pressure sensor 12 corresponds to the diaphragm 22 in which the central portion 22a is formed into a thin film shape with the flow channel thickness T2.

As shown in FIG. 4, an angle formed on a horizontal plane by a pair of straight lines connecting the ends 22b of the diaphragm 22 is represented by $\alpha$. As the angle $\alpha$ increases, an increase of the width of each end 22b per unit length of the flow channel increases. Since a change in the shape and sectional area of the flow channel 21a is small when the angle $\alpha$ is small, the angle $\alpha$ is preferably set to a small value for smooth circulation of the fluid.

On the other hand, when the angle $\alpha$ is small, the width W5 of the central portion 22a of the diaphragm 22 in the center flow channel 28 becomes small. When the width W5 of the central portion 22a of the diaphragm 22 is increased, it is necessary to increase the length of the flow channel of the flow channel body 21. An increase in the length of the flow channel of the flow channel body 21 leads to an increase in the size of the pressure detection device 100.

As the width W5 of the central portion 22a of the diaphragm 22 is set to be closer to the inner diameter of the inflow-side end flow channel 24 and the outflow-side end flow channel 25, the region having the flow channel thickness T2 can be increased. On the other hand, as the width W5 increases, an increase of the width of the end 22b per unit length of the flow channel increases, which may inhibit the smooth circulation of the fluid.

Accordingly, it is preferably to satisfy the following formulas (1) and (2) so as to prevent the length of the flow channel of the flow channel body 21 from being extremely long, while smoothly circulating the fluid.

$$30° < \alpha < 50° \quad (1)$$

$$0.6 < W5/D1 < 1 \quad (2)$$

As shown in FIGS. 7 to 11, when tangential lines are drawn from both ends in the width direction of the diaphragm 22 to a circle in which the inner peripheral surface of the flow channel body 21 is formed, the angles formed by each pair of tangential lines are respectively represented by θ1, θ2, θ3, θ4, and θ5. The values θ1, θ2, θ3, θ4, and θ5 can be arbitrarily set so as to satisfy the formulas (1) and (2). For example, values of 135° to 145°, 85° to 95°, 25° to 35°, and 15° to 25° can be adopted as the values θ1, θ2, θ3, θ4, and θ5.

As shown in FIGS. 7 to 11, the angle formed by a pair of tangential line gradually increases toward the center flow channel 28 from the inflow-side end flow channel 24.

The operation and effects of the pressure detection device 100 of the first embodiment described above will be described.

According to the pressure detection device 100 of the first embodiment, the pair of end flow channels (the inflow-side end flow channel 24 and the outflow-side end flow channel 25) and the center flow channel 28 disposed at a position sandwiched between the pair of end flow channels are integrally formed of a flexible resin material. Accordingly, the flow channel body 21 included in the pressure detection device 100 of the first embodiment has no portion where a part of the portion is sealed with another member, so that a small amount of fluid does not accumulate on the sealed portion. Accordingly, even when a coagulable fluid, such as blood, is circulated, a malfunction that an accumulated and solidified fluid is recirculated through the flow channel can be prevented.

Further, according to the pressure detection device 100 of the first embodiment, the center flow channel 28 includes the diaphragm 22 having a thin film shape, and the diaphragm 12a is disposed in such a manner that the pressure of the fluid circulated through the flow channel 21a is transmitted via the diaphragm 22 having a thin film shape. Therefore, in the pressure detection device 100 of the first embodiment, the diaphragm 12a can appropriately detect the pressure of the fluid transmitted via the diaphragm 22 having a thin film shape.

Thus, according to the pressure detection device 100 of the first embodiment, it is possible to provide the pressure detection device 100 capable of detecting the pressure of the fluid circulated through the flow channel 21a, while preventing the occurrence of a malfunction due to the accumulation of the fluid in the flow channel 21a.

In the pressure detection device 100 of the first embodiment, the center flow channel 28 has a structure in which the distance (flow channel thickness T2) from the inner peripheral surface in a partial region of the center flow channel 28 in the circumferential direction about the axis line Y along the circulation direction is shorter than the distance (flow channel thickness T1) from the inner peripheral surface in another region to the outer peripheral surface, and the partial region is set as the central portion 22a of the diaphragm 22.

With this structure, the partial region of the center flow channel 28 in the circumferential direction can be set as a region in which a displacement due to the pressure of the fluid is more likely to occur than in the other region. The partial region is set as the central portion 22a of the diaphragm 22, thereby making it possible to appropriately detect the pressure of the fluid.

According to the pressure detection device 100 of the first embodiment, the pair of connecting flow channels (the inflow-side connecting flow channel 26 and the outflow-side connecting flow channel 27) connects the pair of end flow channels (the inflow-side end flow channel 24 and the outflow-side end flow channel 25) and the center flow channel 28 so that the flow channel sectional area gradually increases toward the both ends of the center flow channel 28 from the pair of end flow channels. Accordingly, when the fluid is circulated from the inflow-side end flow channel 24, which is disposed at the inflow port 21b, to the center flow channel 28, the fluid does not accumulate on the flow channel 21a. Further, when the fluid is circulated from the center flow channel 28 to the outflow-side end flow channel 25 where the outflow port 24c is disposed, the fluid does not accumulate on the flow channel 21a.

Second Embodiment

Next, a pressure detection device according to a second embodiment of the present disclosure will be described with reference to the drawings.

The second embodiment is a modified example of the first embodiment. The second embodiment is similar to the first embodiment, unless otherwise specified below, and the components of the second embodiment that are similar to those of the first embodiment are denoted by the same reference numerals as those of the first embodiment, and the descriptions thereof are omitted.

Figure 12:
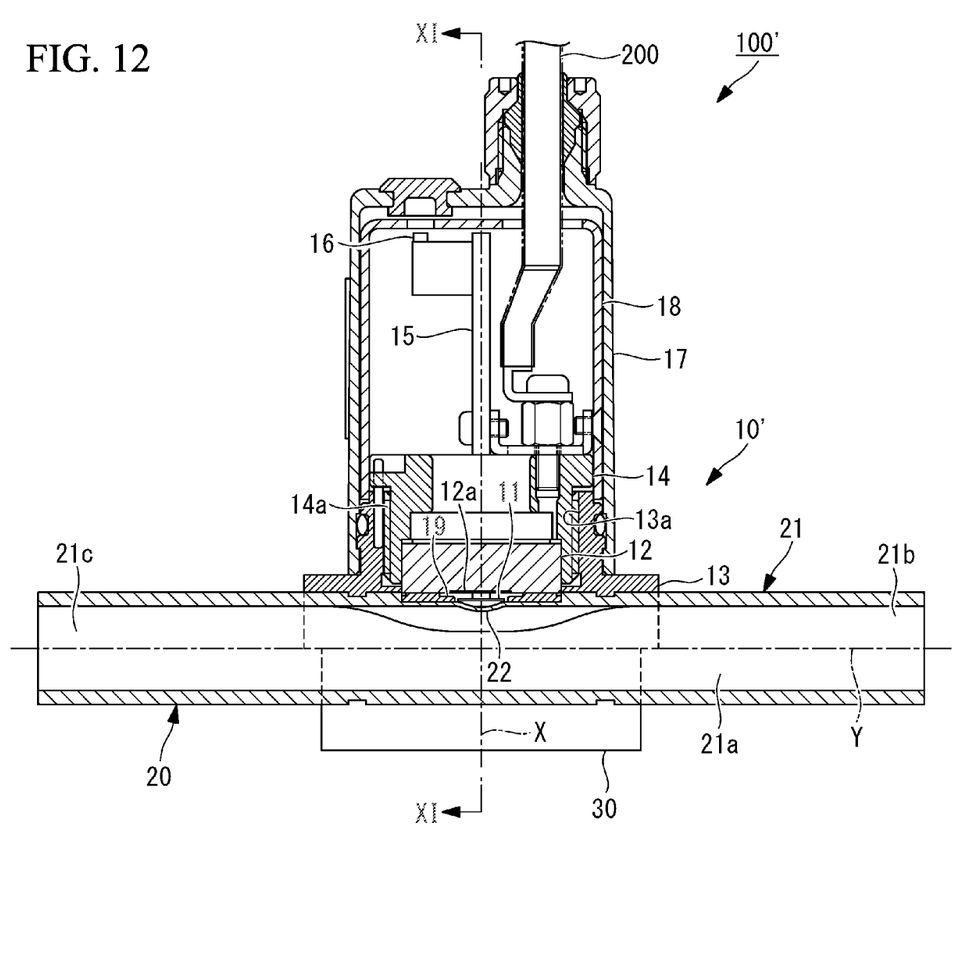
FIG. 12 is a longitudinal sectional view showing a pressure detection device according to a second embodiment.

A pressure detection device 100' of the second embodiment is different from the pressure detection device 100 of the first embodiment in that the pressure transmission portion 11 is disposed between the pressure sensor 12 and the diaphragm 22.

A pressure detection unit 10' included in the pressure detection device 100' shown in FIG. 12 is a device that detects a pressure transmitted to the diaphragm 12a (pressure detection portion).

As shown in FIG. 12, the pressure detection unit 10' includes the pressure transmission portion 11 to which the pressure of the fluid from the diaphragm 22 (pressure receiving portion) of the flow channel unit 20 is transmitted; and a holding member 19 which is disposed between the pressure sensor 12 and the diaphragm 22.

The pressure transmission portion 11 is disposed in a state where an upper end (one end) of the pressure transmission portion 11 along the axis line X is in contact with the diaphragm 12a and a lower end (the other end) thereof along the axis line X is in contact with the diaphragm 22 of the flow channel unit 20. The pressure transmission portion 11 transmits the fluid pressure received by the diaphragm 22 to the diaphragm 12a. Since the pressure transmission portion 11 transmits the fluid pressure to the pressure sensor 12, it is desirable that the pressure transmission portion 11 have a hardness sufficiently higher than that of the diaphragm 22. If the pressure transmission portion has a low hardness, like one used for the diaphragm 22 and the like, the pressure transmission portion serves as a damper that absorbs a pressure, which makes it difficult to measure the pressure accurately.

Figure 13:
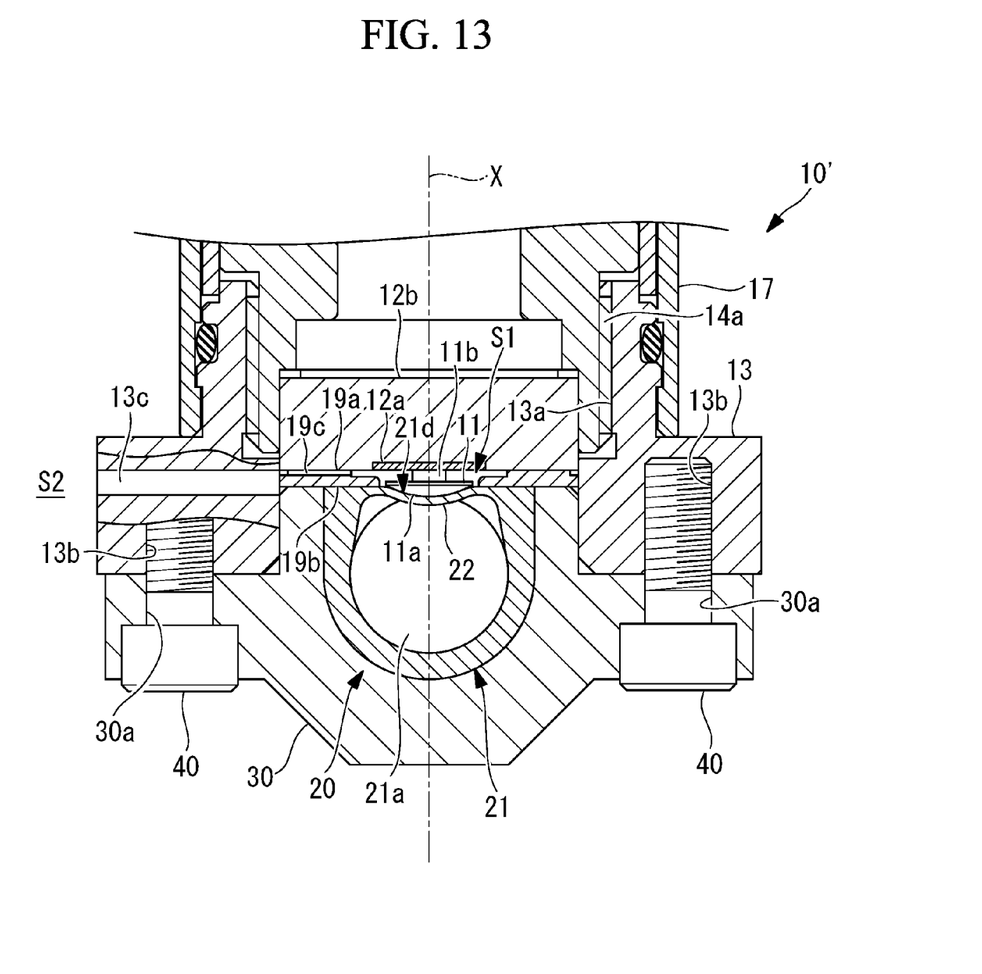
FIG. 13 is a sectional view taken along a line IX-IX of the pressure detection device shown in FIG. 12.

As shown in FIG. 13 (which is a sectional view taken along a line IX-IX of FIG. 12), the pressure transmission portion 11 includes a spherical member 11a (first pressure transmission member) disposed in contact with the diaphragm 22, and a shaft-like member 11b (second pressure transmission member) disposed in contact with the diaphragm 12a. An upper end face of the shaft-like member 11b is connected to the diaphragm 12a with an adhesive. As the adhesive, a material, such as glass, which is melted by heat, is used. When the adhesive is melted by heat and bonded, the adhesive is cooled and hardened. In this case, the adhesive does not serve as a buffering agent, and thus the pressure can be stably measured. Further, an epoxy resin-based adhesive may be used, although the epoxy resin-based adhesive is inferior to glass with which the pressure can be stably measured and which has a high corrosion resistance.

As shown in FIG. 13, the spherical member 11a is a member formed into a spherical shape projecting toward the diaphragm 22 along the axis line X. The shaft-like member 11b is a member formed into a shaft-like shape extending along the axis line X. The spherical member 11a and the shaft-like member 11b are members integrally formed of, for example, metal such as aluminum, PEEK (polyether ether ketone resin), ceramics, or sapphire.

As shown in FIG. 13, a contact area between the upper end face of the shaft-like member 11b and the diaphragm 12a is smaller than a contact area between the spherical member 11a and the diaphragm 22.

The holding member 19 is a member disposed between the pressure sensor 12 and the diaphragm 22 so as to hold the outer peripheral portion of the diaphragm 22, and is formed into an annular shape about the axis line X.

As shown in FIG. 13, one surface 19b at the lower end of the holding member 19 along the axis line X is in contact with the outer peripheral portion of the diaphragm 22, and the other surface 19a at the upper end of the holding member 19 along the axis line X is disposed in a state where the holding member 19 is in contact with the base portion 12b of the pressure sensor 12.

As shown in FIG. 13, the holding member 19 is provided with a vent groove 19c that communicates with an inside space S1 in a state where the pressure sensor 12 is in contact with the holding member 19. The body portion 13 is provided with a vent hole 13c (communication flow channel) that communicates with the vent groove 19c and an outside space S2.

The vent groove 19c and the vent hole 13c allow the inside space S1 and the outside space S2 to communicate with each other. With this structure, the inside space S1 is maintained at the same atmospheric pressure state as that in the outside space S2.

As shown in FIG. 13, in a state where the flow channel unit 20 is attached to the pressure detection unit 10', the diaphragm 22 of the flow channel unit 20 is in contact with the spherical member 11a of the pressure transmission portion 11. An upper end face of the shaft-like member 11b of the pressure transmission portion 11 is connected to the diaphragm 12a.

The diaphragm 22 is disposed on a plane orthogonal to the axis line X in the state where the pressure transmission portion 11 of the pressure sensor 12 is not contact with the diaphragm 22.

On the other hand, as shown in FIG. 13, in the state where the pressure transmission portion 11 is in contact with the diaphragm 22, the diaphragm 22 is in a state where the inner peripheral portion of the diaphragm 22 is displaced downward along the axis line X by the pressure transmission portion 11. In the state shown in FIG. 13, the diaphragm 22 presses the pressure transmission portion 11 upward along the axis line X by an urging force generated by elastic deformation.

In this manner, in the pressure detection device 100' of the second embodiment, the pressure transmission portion 11 displaces the diaphragm 22 toward the flow channel 21a and is disposed in a state of receiving the urging force directed to the diaphragm 12a from the diaphragm 22.

Accordingly, even when the pressure of the fluid in the flow channel 21a becomes a negative pressure which is lower than the atmospheric pressure, the diaphragm 12a can receive the pressure having a value obtained by subtracting the pressure value corresponding to the negative pressure from the pressure value equivalent to the urging force received by the pressure transmission portion 11 from the diaphragm 22.

The operation and effects of the pressure detection device 100' of the second embodiment described above will be described.

According to the pressure detection device 100' of the second embodiment, the pressure transmission portion 11 disposed in such a state where one end of the pressure transmission portion 11 is in contact with the diaphragm 12a of the pressure sensor 12 and the other end thereof is in contact with the diaphragm 22 of the flow channel unit 20 is disposed in a state of receiving the urging force directed to the diaphragm 12a from the diaphragm 22.

Accordingly, even when the pressure of the fluid circulated through the flow channel 21a is temporarily reduced and becomes a negative pressure which is lower than the atmospheric pressure, the diaphragm 12a is in a state of receiving the pressure having a value obtained by subtracting the pressure value corresponding to the negative pressure from the pressure value equivalent to the urging force received by the pressure transmission portion 11 from the diaphragm 22. Thus, even when the pressure of the fluid is temporarily reduced and becomes a negative pressure, the diaphragm 12a can obtain the pressure value by subtracting a decrease in the pressure value due to the negative pressure from the pressure value due to the urging force received from the diaphragm 22.

Thus, according to the pressure detection device 100' of the second embodiment, even when the pressure of the fluid is temporarily reduced and becomes a negative pressure, the pressure of the fluid can be detected accurately.

The pressure detection device 100' of the second embodiment includes the vent groove 19c and the vent hole 13c as a communication flow channel that communicates the inside space S1 and the outside space S2 which are partitioned by the recess 21d and the pressure sensor 12.

With this structure, the inside space S1 which is partitioned by the pressure sensor 12 and the recess 21d in which the diaphragm 22 of the flow channel unit 20 is disposed communicates with the outside space S2. Therefore, it is possible to suppress the occurrence of a malfunction that the volume of the inside space S1 fluctuates according to the displacement of the diaphragm 22 and the pressure of the inside space S1 fluctuates according to the fluctuation in the volume of the inside space S1.

In the pressure detection device 100' of the second embodiment, the contact area between the shaft-like member 11b and the diaphragm 12a is smaller than the contact area between the spherical member 11a and the diaphragm 22.

Accordingly, the fluid pressure received by the spherical member 11a from the diaphragm 22 can be transmitted in such a manner that the fluid pressure is locally concentrated on the diaphragm 12a via the shaft-like member 11b. Therefore, the fluctuation in the pressure locally received by the diaphragm 12a is increased with respect to the fluctuation in the fluid pressure, thereby making it possible to increase the accuracy of detecting the fluctuation in the fluid pressure.

In the pressure detection device 100' of the second embodiment, the spherical member 11a is a member formed into a spherical shape projecting toward the diaphragm 22. Accordingly, a contact area where the spherical member 11a contacts the diaphragm 22 is maintained substantially constant, regardless of the displacement of the diaphragm 22, and thus the accuracy of transmitting the pressure of the fluid from the diaphragm 22 to the spherical member 11a can be increased.

Other Embodiments

In the above description, the pressure sensor 12 is a strain sensor that outputs a pressure signal corresponding to the strain resistance that varies depending on the pressure transmitted to the diaphragm 12a. However, the pressure sensor 12 may have another aspect.

For example, a capacitance pressure sensor may be used.

The invention claimed is:

1. A pressure detection device comprising:
a pressure detection unit configured to detect a pressure to be transmitted to a pressure detection portion; and
a flow channel unit including a flow channel body provided with a flow channel through which a fluid is circulated along a circulation direction from an inflow port to an outflow port, wherein
the flow channel body includes:
a pair of end flow channels disposed at the inflow port and the outflow port, respectively; and
a center flow channel including a pressure receiving portion having a thin film shape and disposed at a position sandwiched between the pair of end flow channels, a distance from an inner peripheral surface of the pressure receiving portion to an outer peripheral surface thereof being shorter than a distance from an inner peripheral surface of the pair of end flow channels to an outer peripheral surface thereof,
the pair of end flow channels and the center flow channel are integrally formed of a flexible resin material, and
the pressure detection portion is disposed in such a manner that the pressure of the fluid circulated through the flow channel is transmitted via the pressure receiving portion.

2. The pressure detection device according to claim 1, wherein
a distance from an inner peripheral surface in a partial region of the center flow channel in a circumferential direction about the circulation direction to an outer peripheral surface thereof is shorter than a distance from an inner peripheral surface in another region of the center flow channel to an outer peripheral surface thereof, and
the partial region is set as the pressure receiving portion.

3. The pressure detection device according to claim 1, wherein
the center flow channel has a flow channel sectional area larger than that of the pair of end flow channels,
a pair of connecting flow channels is formed to connect an end of the pair of end flow channels that is located closer to the center flow channel and both ends of the center flow channel,
the pair of end flow channels, the center flow channel, and the pair of connecting flow channels are integrally formed of a flexible resin material, and
the pair of connecting flow channels is formed in such a manner that a flow channel sectional area of the pair of connecting flow channels gradually increases toward the both ends of the center flow channel.

4. The pressure detection device according to claim 1, wherein
the pressure detection unit includes:
a pressure sensor including the pressure detection portion; and
a pressure transmission portion disposed in a state where one end of the pressure transmission portion is in contact with the pressure detection portion and the other end of the pressure transmission portion is in contact with the pressure receiving portion, the pressure transmission portion being configured to transmit the pressure of the fluid received by the pressure receiving portion to the pressure detection portion, and
the pressure transmission portion displaces the pressure receiving portion toward the flow channel and is disposed in a state of receiving an urging force directed to the pressure detection portion from the pressure receiving portion.

5. The pressure detection device according to claim 4, wherein
the flow channel unit is provided with a recess in which the pressure receiving portion is disposed,
the pressure sensor is disposed in contact with the flow channel unit so as to cover the recess, and
a communication flow channel is formed to allow an inside space and an outside space to communicate with each other, the inside space and the outside space being partitioned by the recess and the pressure sensor.

6. The pressure detection device according to claim 4, wherein
the pressure transmission portion includes:
a first pressure transmission member disposed in contact with the pressure receiving portion; and
a second pressure transmission member disposed in contact with the pressure detection portion, and
a contact area between the second pressure transmission member and the pressure detection portion is smaller than a contact area between the first pressure transmission member and the pressure receiving portion.

7. The pressure detection device according to claim 6, wherein the first pressure transmission member is a member formed into a spherical shape projecting toward the pressure receiving portion.

* * * * *